US00PP18505P3

(12) United States Plant Patent
Layt

(10) Patent No.: US PP18,505 P3
(45) Date of Patent: Feb. 19, 2008

(54) ***DIANELLA CAERULEA* PLANT NAMED 'DCNCO'**

(50) Latin Name: *Dianella caerulea*
Varietal Denomination: DCNCO

(75) Inventor: Todd Anthony Layt, New South Wales (AU)

(73) Assignee: VersaScapes L.L.C., Mt. Pleasant, SC (US)

( * ) Notice: Subject to any disclaimer, the term of this patent is extended or adjusted under 35 U.S.C. 154(b) by 27 days.

(21) Appl. No.: 11/239,579

(22) Filed: Sep. 29, 2005

(65) Prior Publication Data

US 2006/0075534 P1 Apr. 6, 2006

Related U.S. Application Data

(60) Provisional application No. 60/614,804, filed on Sep. 30, 2004.

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

2006/0075534 P1 * 4/2006 Layt ..... Plt./263

OTHER PUBLICATIONS

Royal Horticultural Society Dictionary of Gardening, 1992, volt II D–K, McMillan Press, London; Stockton Press, New York, p. 49–50.*
Layt; "Dianella caerulea blue flax lily 'DCNCO,'" *Plant Varieties Journal* 16 (4): 120 (Feb. 6, 2004).
Layt; "Dianella caerulea blue flax lily 'DCNCO,'" *Plant Varieties Journal* 17 (1): 588–590 (Apr. 28, 2004).
Australian Government, IP Australia, Plant Breeder's Rights; Database entry for Australian Plant Breeders Right Application No. 2003/293; Variety 'DCNCO' http://pbr.i-paustralia.optus.com.au/docs/2003293.doc.

* cited by examiner

*Primary Examiner*—Wendy C. Haas
*Assistant Examiner*—Georgia Helmer
(74) *Attorney, Agent, or Firm*—Myers Bigel Sibley & Sajovec, P.A.

(57) ABSTRACT

'DCNCO' is a distinctive variety of *Dianella caerulea* which is characterized by the combination of its densely tufted, slightly spreading and semi-compact growth habit, pale blue flower colour, a general absence of canes, and a reduced tendency to fall over at maturity.

2 Drawing Sheets

Latin name of the genus and species: The Latin name of the novel variety disclosed herein is *Dianella caerulea.*

Variety denomination: The inventive variety of *Dianella caerulea* disclosed herein has been given the varietal denomination 'DCNCO'.

BACKGROUND OF THE INVENTION

The present invention relates to a new and distinct perennial Blue Flax Lilly variety of *Dianella caerulea,* which has been given the varietal denomination of 'DCNCO'. Its market class is that of an ornamental grass-like plant. 'DCNCO' is intended for use in landscaping and as a decorative grass-like plant.

An application for plant breeders' rights for variety 'DCNCO' has been filed with the Australian Plant Breeders' Rights Office, and was first gazetted in the Plant Varieties Journal in October 2003 under Application No. 2003/293.

Parentage. The *Dianella caerulea* variety 'DCNCO' was first discovered in October 1996 in an Australian nursery in the state of New South Wales after an extensive breeding program. A tall plant height, medium plant density, medium length aerial stems and yellow-green leaf colour characterize the parent of 'DCNCO', 'Sydney Ecotype' (unpatented).

In 1995, *Dianella* species were grown together in an open bed covering approximately 250 square meters of area. They were grown in groups of species and ecotypes including *Dianella caerulea* collected from the Sydney area, and other regions. The other *Dianella* species present were *longifolia, revoluta* and *tasmanica.* The plants were open pollinated with possible assisted pollination from general shaking of flower stems onto each other.

Seeds were collected and sown from the 'Sydney Ecotype' plants in December 1995. Approximately 30,000 plants were grown. In October 1996, using the selection criteria of very short aerial stems (canes) with very short internodes and dense growth habit, a single plant was identified as having an absence of canes. This single plant was selected, potted into a 140 mm pot for further evaluation and named 'DCNCO'.

Asexual reproduction. 'DCNCO' was first asexually propagated by division in April 1997 in the state of New South Wales, Australia. 'DCNCO' was asexually reproduced again during November 1997 and April 1998 and confirmed to be stable in character. The distinctive characteristics of the inventive variety, 'DCNCO', have remained stable and true to type from generation to generation through successive cycles of asexual reproduction including vegetative division and micropropagation.

'DCNCO' has a densely tufted, slightly spreading and semi-compact growth habit, with a general absence of canes, which is unusual for a *Dianella caerulea,* particularly when compared to the 'Sydney Ecotype'. 'DCNCO' also has been observed to be less prone to falling over than the parent type.

SUMMARY OF THE INVENTION

'DCNCO' is a distinctive variety of *Dianella caerulea* which is characterized by the combination of its densely tufted, slightly spreading and semi-compact growth habit, pale blue flower colour, a general absence of canes, and a reduced tendency to fall over at maturity.

BRIEF DESCRIPTION OF THE FIGURES

The photographs in the drawings were made using conventional techniques and show the colours as true as reasonably possible by conventional photography. Colours in the photographs may differ slightly from the colour values cited in the detailed botanical description, which accurately describe the colours of the new *Dianella caerulea.*

BOTANICAL DESCRIPTION OF THE PLANT

The following is a detailed botanical description of a new and distinct variety of a *Dianella caerulea* ornamental grass-like plant known as 'DCNCO'. The descriptions disclosed herein are based upon observations of the plant grown in 140 mm nursery pots and field plots in New South Wales, Australia. The plants were approximately 12-months-old at the time of observation. All colors cited herein refer to The Royal Horticultural Society Colour Chart (The Royal Horticultural Society, London, 2001 edition).

Those skilled in the art will appreciate that certain characteristics will vary with older or, conversely, younger plants. 'DCNCO' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like.

Figure 1:
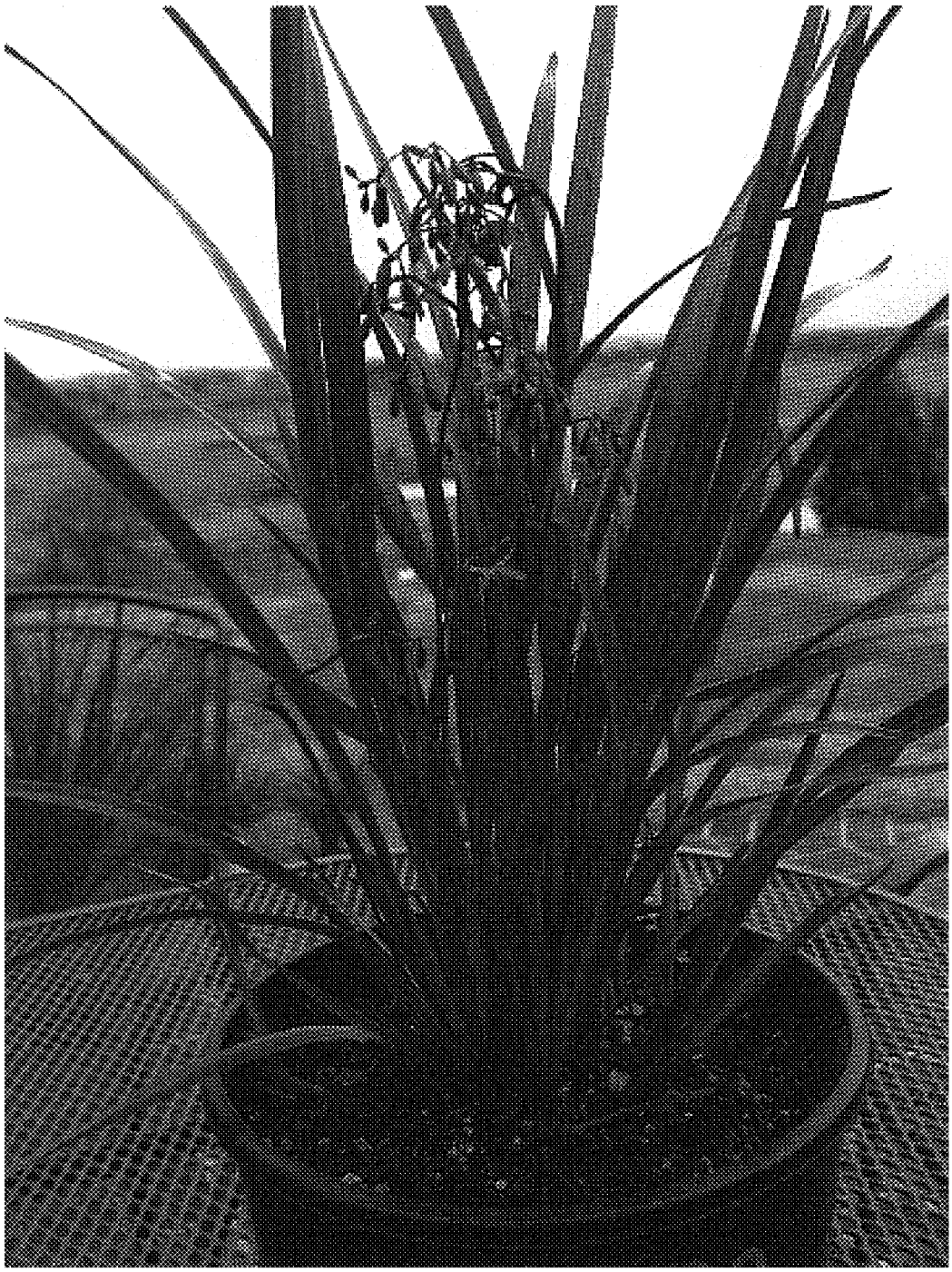
FIG. 1 shows a 'DCNCO' plant, and illustrates the absence of canes, low to medium height of inflorescence, and semi-compact clump that are characteristic of the variety.
Figure 2:
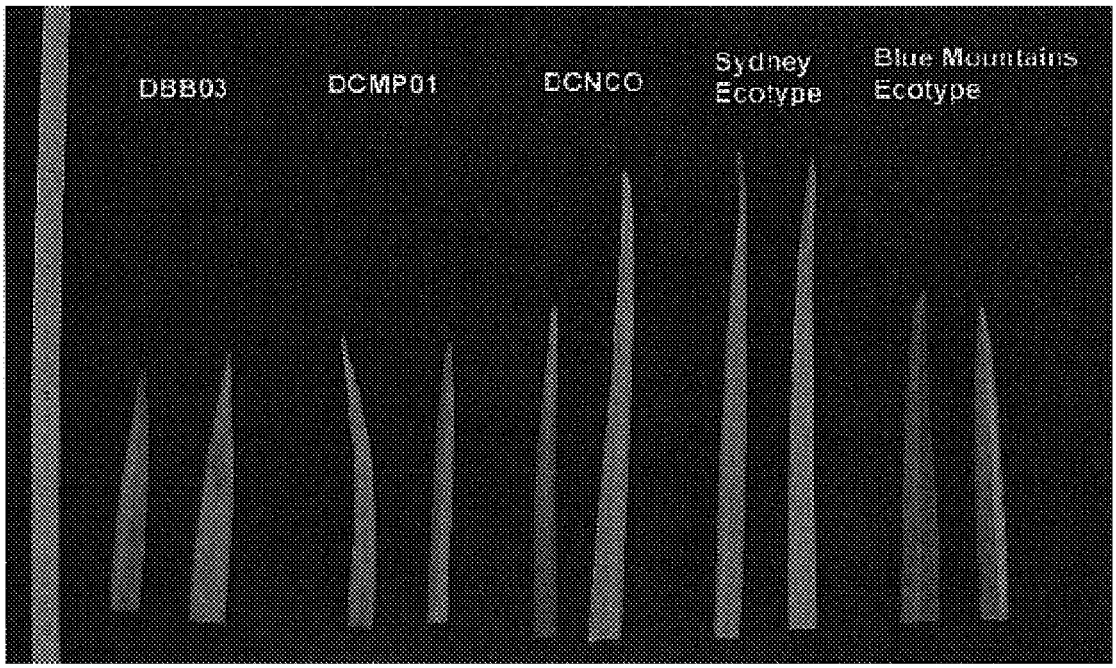
FIG. 2 shows the variation in leaf width and glaucosity among the five *Dianella caerullea* varieties included in the comparison study.

'DCNCO' is a perennial *Dianella caerulea* plant which was produced through an innovative breeding program. After its selection, 'DCNCO' was asexually propagated by division and micropropagation. 'DCNCO' has a densely tufted, slightly spreading and semi-compact growth habit, with a general absence of canes, which is unusual for *Dianella caerulea.* A botanical description of 'DCNCO' and a comparison with other varieties of *Dianella caerulea* are provided below. A representative *Dianella caerulea* 'DCNCO' plant is illustrated in FIG. 1.

Technical Description of the Variety.

Growth Habit. 'DCNCO' is a rhizomatous plant forming a semi-compact tussock. It has an erect growth habit, its height is tall (mean 65.6 cm) and the density of its shoots medium-strong.

Stem. Length of internodes is short (less than 10 mm). The Sydney ecotype has internode length which is long (greater than 20 mmm) creating long aerial stem length (also known as canes).

Foliage. Leaf attitude erect, width medium (mean 13.6 mm), upper side colour with waxiness removed yellow-green (RHS 147B), lower side colour with waxiness removed yellow-green (RHS 147B), upper side glaucosity weak, shape ligulated, apex acute, cross section slightly concave, cross-sectional shape with midrib keeled, spines on margin present with medium prominence, spines on lower side midrib present with medium prominence.

Basal shoots. Red/green and light brown in color.

Basal sheath. Anthocyanin colour red-brown (RHS 178A to 182A fading to 182B), intensity of anthocyanin colour medium.

Inflorescence. Inflorescence (flower spike) is pale blue (approximately RHS 93D) with an average length compared to other *Dianella caerulea.* The flower spike is soft to the touch, a panicle with a length in a range from 80-90 cm. The inflorescence is positioned above the level of the foliage. The flower spike is soft to the touch. Peduncle color is yellow green (approximately RHS 146B-C). Flowering season is late spring-summer.

Flowers: The flower buds are 8-10 mm long and 3-4 mm wide. Bud color changes from yellow green (RHS 146B) to violet blue (approximately RHS 90A-93D) prior to opening. Mature flowers have 6 petals with ovate shape. Petal color is violet-blue (approximately RHS 97C) along the centre and violet-blue (approximately RHS 96B) along the margin. Anther filament color is yellow (RHS 6A) and yellow orange (approximately RHS 14A). Flower diameter range is 9-13 mm. Petal attitude is reflexed.

Fruit: A succulent berry, length to 11 mm, shape is globose, sometimes asymmetrical, color of unripe berry is yellow green (RHS 146A) and color of ripe berry is approximately violet blue (RHS 89A), surface texture is smooth and glossy. Seed color is black.

Environmental Tolerances. 'DCNCO' has shown potential for shade tolerance. The winter hardiness of 'DCNCO' is at least to −10 degrees Celsius. 'DCNCO' has been observed to hold color to −7 degrees Celsius. 'DCNCO' has good color retention in winter compared with other known varieties of *Dianella caerulea,* with one known exception of 'DBB03', which has better winter color retention than 'DCNCO'.

'DCNCO' has excellent drought tolerance compared with other *Dianella caerulea* varieties; this is most likely due to the massive root system. After severe wilting, 'DCNCO' has been noted to recover with watering.

Disease Resistance and Susceptibility. 'DCNCO' has excellent tolerance to pests and diseases and good resistance to root rot, which is a common problem in *Dianella caerulea.* Root rot is caused by the disease causing organism *Phytophthora.* Tolerance to pests can refer to no damage from snails, slugs, mites, aphids, whitefly, beetles, caterpillars and moths.

These features and other characteristics of the plant are apparent from the figures.

'DCNCO' Compared to Other Varieties of *Dianella caerulea.*

Grouping characteristics used to identify the most similar varieties of common knowledge to 'DCNCO' were tall plant height and dense growth habit. Based on this the parent ('Sydney Ecotype') was selected as the most similar suitable comparator. Other *D. caerulea* used in the comparative trial included 'Blue Mountains Ecotype' (unpatented), a form from the Blue Mountains region of New South Wales, 'DBB03' (U.S. Provisional Application No. 60/614,654 filed Sep. 30, 2004; Australian Plant Breeders Rights Application No. 2003/291, received Oct. 8, 2003) and 'DCMP01' (U.S. Provisional Application No. 60/614,658, filed Sep. 30, 2004;

Australian Plant Breeders Rights Application No. 2003/292, received Oct. 8, 2003).

The comparative trial of *Dianella caerulea* 'DCNCO' with the other *D. caerulea* was conducted in open beds in Summer 2002 through Autumn 2003 in Clarendon, New South Wales, Australia. The plants for this trial were propagated from divisions and planted into 130 mm pots filled with soilless potting mix. Nutrition was maintained with slow release fertilizers and pest and disease treatments were applied as required. The plants did not flower during the trial. Trial design included fifteen pots of each variety arranged in a completely randomized design. Measurements were taken from ten plants at random with one sample taken per plant.

In comparing 'DCNCO' with other *D. caerulea,* 'DCNCO' has a more compact habit than 'Sydney Ecotype', 'Blue Mountains Ecotype' and 'DBB03' and a less compact form compared to 'DCMP01'. Similar to 'DBB03', canes are generally absent from 'DCNCO', whereas 'DCMP01' has compact canes above the ground, and the 'Sydney Ecotype' has canes of typical length above the ground. 'DCNCO' has a medium flower spike height compared to 'DCMP01', which has a medium to tall flower spike height, whereas 'DBB03' has a tall flower spike height, and the 'Sydney Ecotype' has a variable flower spike height. 'DCNCO' has pale blue flower colour, whereas 'DCMP01' has a deeper blue almost purplish flower colour, and the 'Sydney Ecotype' flower colour is variable. Further comparisons are presented in Table 1 below.

TABLE I

Comparison of *Dianella caerulea* varieties.

| | 'DBB03' | 'DCMP01' | 'DCNCO' | Sydney ecotype | Blue Mountains ecotype |
|---|---|---|---|---|---|
| PLANT: GROWTH HABIT | | | | | |
| | erect | erect | erect | erect to semi-erect | semi-erect to erect |
| PLANT HEIGHT (cm) LSD (P ≦ 0.01) = 6.03 | | | | | |
| mean | 23.4[c] | 24.6[c] | 65.6[a] | 63[a] | 49.4[b] |
| std deviation | 2.2 | 2.6 | 5 | 5.5 | 8.5 |
| PLANT: DENSITY OF SHOOTS | | | | | |
| | strong | strong | medium-strong | medium | weak |
| STEM: INTERNODE LENGTH | | | | | |
| | short | short | short | long | very long |

TABLE I-continued

Comparison of *Dianella caerulea* varieties.

| | 'DBB03' | 'DCMP01' | 'DCNCO' | Sydney ecotype | Blue Mountains ecotype |
|---|---|---|---|---|---|
| LEAF: WIDTH (mm) LSD (P ≦ 0.01) = 1.97 | | | | | |
| mean | 14.9[c] | 12.2[d] | 13.6[cd] | 17.1[b] | 22.2[a] |
| std deviation | 2.1 | 0.6 | 0.8 | 0.9 | 2.9 |
| LEAF: FOLIAGE COLOUR - overall appearance of leaf | | | | | |
| | blue-green | yellow-green | yellow-green | yellow-green | yellow-green |
| LEAF: COLOUR (RHS 2001) - waxiness removed | | | | | |
| upper side | 147A | 147A | 147B | 146B | ca 147A |
| lower side | 147A | 147B | 147B | 1468 | 147B |
| LEAF: GLAUCOSITY | | | | | |
| | strong | weak | weak | weak | weak |
| LEAF: CROSS SECTION | | | | | |
| | concave | concave | slight concave | slight concave | concave |
| LEAF: PRESENCE OF SPINES ON MARGIN | | | | | |
| | absent | absent | present | present | present |
| LEAF: PROMINENCE OF SPINES ON MARGIN | | | | | |
| | n/a | n/a | medium | medium | very weak |
| LEAF: PRESENCE OF SPINES ON LOWER SIDE MIDRIB | | | | | |
| | absent | absent | present | present | present |
| LEAF: PROMINENCE OF SPINES ON LOWER SIDE MIDRIB | | | | | |
| | n/a | n/a | medium | medium | medium |
| BASAL SHEATH: COLOUR | | | | | |
| | blue-green | red-brown | red-brown | brown to red-brown | red to red-brown |
| BASAL SHEATH: INTENSITY OF ANTHOCYANIN COLOUR | | | | | |
| | absent | weak | medium | medium | strong |

Mean values followed by the same letter are not significantly different at P ≦ 0.01 according to an S-N-K test.

That which is claimed is:

1. A new and distinct variety of *Dianella caerulea* plant named 'DCNCO', substantially as described and illustrated herein.

* * * * *